US005578302A

United States Patent [19]

Brassart et al.

[11] Patent Number: 5,578,302
[45] Date of Patent: Nov. 26, 1996

[54] TREATMENT OF STOMACH ULCERS

[75] Inventors: Dominique Brassart, Bussigny; Pierre Michetti; Jean-Richard Neeser, both of Lausanne, all of Switzerland

[73] Assignee: Nestec S.A., Vevey, Switzerland

[21] Appl. No.: 430,297

[22] Filed: Apr. 28, 1995

Related U.S. Application Data

[63] Continuation of Ser. No. 84,528, Jun. 29, 1993, abandoned.

[30] Foreign Application Priority Data

Jul. 6, 1992 [EP] European Pat. Off. .............. 92810515

[51] Int. Cl.$^6$ .............................. A01N 63/00; C12N 1/20; A23L 1/28
[52] U.S. Cl. ...................... 424/93.45; 435/252.9; 435/853; 435/854; 426/61
[58] Field of Search ................................ 435/252.9, 854, 435/853; 424/93.45; 426/61, 583, 587, 588, 580

[56] References Cited

U.S. PATENT DOCUMENTS

| 3,953,609 | 4/1976 | Farr | 426/2 |
|---|---|---|---|
| 4,314,995 | 2/1982 | Hata et al. | 424/93 |
| 4,332,790 | 6/1982 | Sozzi et al. | 424/38 |
| 4,689,226 | 8/1987 | Nurmi et al. | 424/93 |
| 4,839,281 | 6/1989 | Gorbach et al. | 435/34 |
| 4,921,857 | 5/1990 | Heck et al. | 514/254 |
| 4,946,791 | 8/1990 | Manfredi et al. | 435/252.9 |
| 4,980,164 | 12/1990 | Manfredi et al. | 424/93 |
| 4,985,246 | 1/1991 | Okonogi et al. | 424/115 |
| 5,032,399 | 7/1991 | Gorbach et al. | 424/93 |
| 5,116,821 | 5/1992 | Randall et al. | 514/25 |
| 5,214,053 | 5/1993 | Nakazawa et al. | 514/318 |
| 5,229,380 | 7/1993 | Harris | 514/152 |
| 5,256,425 | 10/1993 | Herman et al. | 424/93 |

FOREIGN PATENT DOCUMENTS

| 199535A2 | 10/1986 | European Pat. Off. . |
|---|---|---|
| 8905849 | 6/1989 | WIPO . |
| 9109608 | 7/1991 | WIPO . |

OTHER PUBLICATIONS

Gismondo, M. R., et al., "Clin. TO.," vol. 134, 1990, pp. 41–46 plus English translation.

Bazzoli, R. M. et al., "Gastroenterology", vol. 102 (4, part 2), Abstracts, p. A 38, Apr. 1992.

Bhatia, S. J., et al., "J. of Clin. Microbiology." vol. 27(10), Oct. 1989, pp. 2328–2330.

Midolo, P. D., et al., "Gastroenterology," Supplement, vol. 104 (4 part 2), Abstracts p. A746, Apr. 1993.

Berg, et al., Immune Responses of Specific Pathogen–Free and Gnotobiotus Mice to Antigens of Indigenous and Non–indigenous Microorganisms. Infection and Immunity, vol. 11, Feb. 1975, pp. 320–329.

Shahani, et al., Role of dietary lactobacilli in gastrointestinal microecology. The American Journal of Clinical Nutrition. Vol 33, Nov. 1980, pp. 2448–2457.

Hotta, et al., Clinical Effects of Bifidobacterium Preparations on Pediatric Intractable Diarrhea. Keio J. Med. pp. 298–314, 1987.

Driessen, et al., Fermented milks with selected intestinal bacteria: a healthy trend in new products. Neth Milk Dairy J. 43 (1989) 367–382.

Perdigon, et al., Prevention of gastrointestinal infection using immuno–biological methods with milk fermented with lactobacillus casei and lacto–bacillus acidophilus. J. of Dairy Research. 57, (1990), 255–264.

Goldin, et al., Survival of Lactobacillus Species (Strain GG) in Human Gastrointestinal Tract. Digestive Diseases and Sciences. Vol. 37, No. 1 (Jan. 1992) pp 121–128.

Coconnier, et al., Protein–Mediated Adhesion of Lactobacillus acidophilus BG2F04 on Human Enterocyte and Mucus–Secreting Cell Lines in Culture. Applied and Environ. Micro., vol. 58, No. 6, Jun. 1992, pp. 2034–2039.

Chauvière, et al., Competitive exclusion of diarrheagenic Escheria coli (ETEC) from human enterocyte–like Caco–2 cells by heat–killed Lactobacillus. FEMS Microbiology Letters 91 (1992) 213–218.

Biological Abstract No. 252134 (vol. 79):Ducluzeau, et al., "Transfer of the Fecal Microbial Flora From Holoxenic Piglets and Adult Pigs to Axenic Piglets and Axenic Adult Mice; Effect of the Animal Host and of the Diet on the Fecal Microbial Pattern of these Animals". *Ann Microbial* (Paris). 1978, pp. 597–612. vol. 129B.

Perdigón, et al., "Actividad Inmunopotenciadora de Bacterias Lacticas Administradas por Via Oral". *Medicina* (Buenos Aires). 46 (1986): 751–754 (with translation).

Silva, et al., "Antimicrobial Substance from a Human Lactobacillus Strain". *Antimicrobial Agents and Chemotherapy*. Aug., 1987, 31(8), pp. 1231–1233.

Patent Abstracts of Japan (vol. 13, No. 579): JP–A–12 42 532, Yasui Hisako, et al., Sep. 27, 1989.

Medline Database Abstract No. 92253433:Balli, et al., "Batterioterapia orale ad alte dosi nella diarrea cronica a spacificia del bambino". *Pediatr Med Chir* (Italy). Jan.–Feb., 1992, 14(1), pp. 13–15.

Perdigón, et al., "Systemic Augmentation of the immune response in mice by Feeding Fermented milks with Lactobacillus casei and Lactobacillus acidophilus". *Immunology*. 63 (1988): pp. 17–23.

Pinto, et al., "Enterocytic Differentiation of Cultured Human Colon Cancer Cells By Replacement of Glucose By Galactose in the Medium," *Biol. Cell.* 44 (1982): 193–196.

*Primary Examiner*—Michael G. Wityshyn
*Assistant Examiner*—Kristin K. Larson
*Attorney, Agent, or Firm*—Vogt & O'Donnell, LLP

[57] ABSTRACT

Stomach ulcers are treated by administering orally to a human in need thereof an anti-*Helicobacter pylori* effective amount of a composition containing, in combination with an ingestible support, a culture of *Lactobacillus johnsonii* strain CNCM I-1225 or a supernatant phase isolated from a culture of *Lactobacillus johnsonii* strain CNCM I-1225.

3 Claims, No Drawings

TREATMENT OF STOMACH ULCERS

CROSS-REFERENCE TO RELATED APPLICATIONS

This application is a continuation application of application Ser. No. 08/084,528, filed Jun. 29, 1993, now abandoned.

BACKGROUND OF THE INVENTION

This invention relates to an antigastritis and/or antiulcer agent and to a lactic acid bacterium strain capable of producing this agent.

It is known that certain lactic acid bacterium strains show good adhesion to intestinal cells and, by virtue of this property, lend themselves to therapeutic applications.

European Patent Application Publication No. 199,535 (Gorbach and Goldin), for example, proposes a Lactobacillus strain named GG after its inventors and deposited in the ATCC (American Type Culture Collection) under No. 53103 which is intended to be administered to human beings or to animals for therapeutic or prophylactic treatment of the digestive tract.

The problem addressed by the present invention was to provide an antigastritis and/or antiulcer agent and a lactic acid bacterium strain capable of producing this agent which could be administered to human beings or to animals for therapeutic or prophylactic treatment of the stomach and particularly the pylorus.

SUMMARY OF THE INVENTION

To this end, the present invention relates to an antigastritis and/or antiulcer agent which is capable of displacing pathogenic bacteria from intestinal and/or gastric cells, to a biologically pure culture of a lactic acid bacterium strain selected for its ability to produce this agent and to a composition containing an effective quantity of the agent or the culture mentioned and an ingestible support, more particularly a pharmaceutically acceptable support and/or a food product, such as an acidified milk, more particularly a yogurt or a milk-based powder formulation.

DETAILED DESCRIPTION OF THE INVENTION

It has been found that certain strains of lactic acid bacteria particularly strains of *Lactobacillus acidophilus,* are capable of displacing pathogenic bacteria, such as *Heliobacter (H.) pylori* for example, from the intestinal cells to which they adhere. It has also been found that the strains in question have the ability to produce an agent showing such power of displacement and, above all, to produce it in their culture medium.

Accordingly, the agent, the strain and the composition according to the invention are more particularly intended for administration to human beings or animals for therapeutic or prophylactic treatment of the stomach and particularly for the treatment of gastritis or ulcers of the stomach or the pylorum.

Among the various strains selected in accordance with the present invention, one was deposited by way of example under the Budapest Treaty on the Jun. 30, 1992 at the Collection Nationale de Microorganismes (CNCM), Institut Pasteur, 28 rue du Dr Roux, 75724 Paris Cedex 15, France, where it was given the No. *Lactyobacillus acidophilus* strain CNCM I-1225.

Subsequent to deposit of strain CNCM I-1225, the taxonomic classification of *Lactobacillus acidophilus* was reorganized to include six subgroups or "genomospecies." See Fujisawa, et al., Taxonomic Study of the *Lactobacillus acidophilus* Group with Recognition of *Lactobacillus gallinarum* sp nov and *Lactobacillus johnsonii* sp nov and Synonymy of *Lactobacillus acidophilus* Group A3 with the Type Strain of *Lactobacillus amylovorous,* Int. J. Syst. bacteriol. 42:487–491 (1992). Subsequent to that taxonomic reclassification, it was determined that strain CNCM I-1225 is a member of the newly established *Lactobacillus johnsonii* species.

Details of the morphology and general properties of this strain are given in the following:

Morphology

Gram-positive microorganism, non-motile, non-sporing. Fairly short and thick rodlets.

Metabolism

Microaerophilic microorganism with homofermentative metabolism giving rise to the production of L(+) and D(−) lactic acid.

Other characteristics: catalase (−), production of $CO_2$ (−), hydrolysis of arginine (−).

Fermentation of sugars

Amygdaline (+), arabinose (−), cellobiose (+), esculine (+), fructose (+), galactose (+), glucose (+), lactose (+), maltose (+/−), mannitol (−), mannose (+), melibiose (−), raffinose (+), ribose (−), salicine (+), sucrose (+), trehalose (+).

Details of the particular properties for which the present strain may be selected are given in the following:

Adhesion

Adhesion to gastric cells may be compared with adhesion to intestinal cells providing the receptors recognized by a microorganism on the two types of cells are similar and the microorganism shows strong power of adhesion to the two types of cells.

Certain pathogenic microorganisms, such as *Heliobacter pylori* for example, seem to have this property.

It may be verified in particular that *Helicobacter pylori* is capable of adhering to human intestinal cells derived from adenocarcinomas, for example the HT29 cells (Pinto et al., Biol. Cell. 55, 193–196, 1982), in a monolayer culture in vitro.

To this end, the HT29 cells are cultured at 37° C. in Dulbeccos modified Eagle medium (DMEM) containing 10% galactose and dialyzed calf serum in an atmosphere of 10% $CO_2$ and 90% air and are used before the 20th culture passage. The cultures are performed on degreased glass slips placed in 24-cup trays.

*H. pylori* is cultured on Müller-Hinton plates, 10% sheep's blood, for 72 h at 37° C. in an atmosphere of 5% $O_2$, 10% $CO_2$ and 85% nitrogen. The plates are scraped and the bacteria are collected and then washed in physiological solution.

*H. pylori* is inoculated onto the HT29 cells in a quantity of $10^6$ viable germs or cells (cfu) per $cm^2$. The whole is then incubated for 2 h at 37° C. and the monolayers are washed three times.

The number of *H. pylori* cells adhering to the HT29 cells is determined by a urease test (Jatrox-Hp-Test) of which the principle is that an aqueous solution of urea and phenol red changes color from yellow to fuschia pink in the presence of urease which catabolizes the production of basic metabolites of urea, ammonium and bicarbonate. The intensity of the reaction is read off from a spectrophotometer at 550 nm. This test is linear for values of $10^4$ to $10^6$ cfu/ml.

Displacement

To determine the ability of a strain, culture, agent or composition according to the invention to displace pathogenic bacteria, the extent to which it is capable of displacing the *H. pylori* adhering to the HT29 cells, for example, may be examined.

To this end, a solution or suspension of the lactic acid bacterium to be selected or agent to be tested may be added to the HT29 cells to which the *H. pylori* cells adhere, after which the whole is incubated for 1 h and washed several times before the urease test is performed.

If a culture of the *L. johnsonii* strain CNCM I-1225, for example, is added with its culture medium (MRS or milk for example), 50% diluted with DMEM, and is added in a quantity of $10^7$ cfu per cm$^2$, it is found that, of the $2 \times 10^6$ cfu/cm$^2$ of adhering *H. pylori* in the absence of competitive bacteria, only $6 \times 10^3$ cfu/cm$^2$ remain after incubation for 1 h with the *L. johnsonii* strain CNCM I-1225.

This demonstrates the advantage which such a strain can have in the treatment of gastritis or ulcers of the stomach or pylorum.

Similarly, if the supernatant phase of the above *L. johnsonii* culture is added to the HT29 cells to which the *H. pylori* cells adhere, a very pronounced displacement of *H. pylori* is again observed. This shows that certain strains of lactic acid bacteria, in the present case the *L. johnsonii* strain CNCM I-1225, are capable of secreting an antigastritis and/or antiulcer agent in their culture medium. Accordingly, the supernatant phase and the agent extracted therefrom may themselves be of considerable advantage in the treatment of gastritis or ulcers of the stomach or the pylorum.

We claim:

1. A method for treating stomach ulcers comprising administering orally to a human in need thereof an anti-*Helicobacter pylori* effective amount of a composition containing, in combination with an ingestible support, a culture of *Lactobacillus johnsonii* strain CNCM I-1225 or a supernatant phase isolated from a culture of *Lactobacillus johnsonii* strain CNCM I-1225.

2. A method according to claim 1 wherein the composition is in the form of an acidified milk product.

3. A method according to claim 1 wherein the composition is in the form of a yogurt.

\* \* \* \* \*